(12) United States Patent
Wada

(10) Patent No.: US 9,662,005 B2
(45) Date of Patent: May 30, 2017

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Manabu Wada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 66 days.

(21) Appl. No.: 14/518,991

(22) Filed: Oct. 20, 2014

(65) Prior Publication Data

US 2015/0116662 A1 Apr. 30, 2015

(30) Foreign Application Priority Data

Oct. 24, 2013 (JP) .................................. 2013-221090

(51) Int. Cl.
*A61B 3/14* (2006.01)
*A61B 3/00* (2006.01)
*A61B 3/10* (2006.01)
*A61B 3/117* (2006.01)

(52) U.S. Cl.
CPC ............ *A61B 3/0025* (2013.01); *A61B 3/102* (2013.01); *A61B 3/117* (2013.01); *A61B 3/14* (2013.01)

(58) Field of Classification Search
CPC ...... A61B 3/0025; A61B 3/102; A61B 3/1025; A61B 3/1233; A61B 3/14; A61B 3/145
USPC .................................. 351/205, 206, 221, 246
See application file for complete search history.

(56) References Cited

U.S. PATENT DOCUMENTS

2012/0140172 A1* 6/2012 Torii ...................... A61B 3/102
351/206

FOREIGN PATENT DOCUMENTS

JP 5199031 B2 5/2013

* cited by examiner

*Primary Examiner* — Huy K Mai
(74) *Attorney, Agent, or Firm* — Canon U.S.A. Inc., IP Division

(57) ABSTRACT

In pattern matching for detecting a positional difference between tomographic images of an eye to be examined, a target within the eye to be examined which causes a reduction in the similarity even though there is no positional difference, is selectively excluded.

28 Claims, 10 Drawing Sheets

IMAGE PROCESSING APPARATUS, IMAGE PROCESSING METHOD, AND PROGRAM

BACKGROUND OF THE INVENTION

Field of the Invention

The present invention relates to an image processing apparatus, an image processing method, and a program.

Description of the Related Art

Optical interference tomography apparatuses based on optical coherence tomography (OCT) utilizing multi-wavelength light wave interference are used in ophthalmology. Optical interference tomography apparatuses apply measuring light, which is low-coherent light, to an eye to be examined, and measure reflected scattered light from the eye to be examined by utilizing an interference system. By scanning the measuring light over the eye to be examined, a tomographic image of the eye to be examined can be captured with high resolution.

Various noises are generated in a tomographic image of an eye to be examined captured with such an optical interference tomography apparatus. A noise reduction is achieved by performing averaging processing on plural tomographic images captured for the same region. In addition, because involuntary eye movement of an eye to be examined prevents photographing of exactly the same region, as preprocessing to be performed for averaging processing on plural tomographic images, detection of a positional difference between the plural tomographic images and correction of the positional difference by translation and rotation of all the tomographic images, are performed. Detection of a positional difference will be explained below in detail. Calculating similarities (or differences) among plural tomographic images using pattern matching and obtaining the positional relationship between the tomographic images having the highest similarity (or lowest difference), is a general method for detecting a positional difference.

An ophthalmological photographing apparatus, which provides a high-definition tomographic image by performing high-accuracy detection of a positional difference and high-accuracy correction of the positional difference, has been suggested. In a technique disclosed in Japanese Patent No. 5199031, a tomographic image is divided into plural regions and pattern matching is performed for each of the plural regions. Accordingly, detection of a positional difference and correction of the positional difference can be performed for each divided region, and an excellent tomographic image can be obtained for which a local positional difference within a single tomographic image has been coped with.

An eye to be examined contains a macular portion and an optic disk rim portion. When such an eye to be examined is photographed with an optical interference tomography apparatus, pulsation of blood vessels, such as constriction and dilation, causes the image brightness of a blood vessel portion in a tomographic image to change. Further, since the optic disk rim portion is a portion where the incidence angle of measuring light relative to a target applied from the optical interference tomography apparatus is large, reflected scattered light which is directed from the eye to be examined towards the optical interference tomography apparatus is weak. Accordingly, the image brightness of the optic disk rim portion in the tomographic image is low and susceptible to noise.

A case where, in order to reduce noise, averaging processing is performed on plural tomographic images captured for the same region including such a blood vessel portion or optic disk rim portion, will be discussed below.

Regarding portions other than the blood vessel portion and the optic disk rim portion in a tomographic image, in the case where there is a positional difference between tomographic images, the similarity calculated by pattern matching is low. Meanwhile, in the case where there is no positional difference between tomographic images, the similarity calculated by pattern matching is high.

In contrast, regarding the blood vessel portion and the optic disk rim portion, since these portions are susceptible to a brightness change and noise, even if there is no positional difference between tomographic images, the similarity is low. It is therefore difficult to distinguish between the case where there is a positional difference and the case where there is no positional difference.

Although there is no case where only the blood vessel portion or the optic disk rim portion exists in a template, there are many cases where such a portion is included in a template. In such cases, similarities calculated by pattern matching are somehow influenced by the reduction in similarity attributable to the blood vessel portion or the optic disk rim portion. The influence of the reduction in similarity depends on the proportion of the blood vessel portion or the optic disk rim portion in a region in a template.

As a result, a tomographic image becomes blurred by performing averaging processing in a state where the number of tomographic images to be subjected to averaging processing is not increased or a state where a positional difference between tomographic images is not correctly detected.

In the case where a template is divided into plural regions and a positional difference is detected, as in Japanese Patent No. 5199031, the division into the plural regions generates a region with a large proportion of the blood vessel portion or the optic disk rim portion in the divided region. Therefore, a situation occurs frequently in which the number of tomographic images on which averaging processing has been performed is small or a tomographic image partially blurs.

SUMMARY OF THE INVENTION

The present invention describes solutions for the above-mentioned shortcomings of conventional technology.

An image processing apparatus according to an aspect of the present invention includes an acquiring unit configured to acquire a first tomographic image and a second tomographic image; a determining unit configured to determine similarity by comparing the first tomographic image, which includes plural regions, with the second tomographic image, which includes plural regions, for each of the plural regions; a selecting unit configured to select at least one of similarities in the plural regions, on the basis of the similarities; and a registration unit configured to perform registration between the first tomographic image and the second tomographic image, on the basis of the similarity selected by the selecting unit.

Further features of the present invention will become apparent from the following description of exemplary embodiments with reference to the attached drawings.

DESCRIPTION OF THE EMBODIMENTS

First Embodiment

Figure 1:
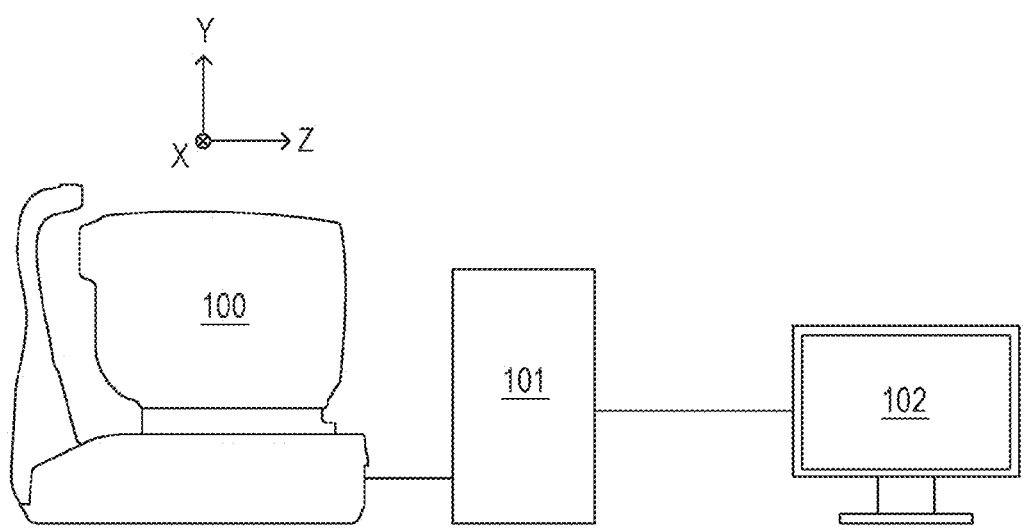
FIG. 1 is a diagram illustrating an example of a configuration of an optical interference tomography apparatus.

Hereinafter, a first embodiment of the present invention will be described with reference to attached drawings. FIG. 1 is a diagram illustrating a configuration of an optical interference tomography apparatus (ophthalmological apparatus) according to a first embodiment.

The optical interference tomography apparatus includes a data acquisition unit 100 which acquires image data by scanning and capturing of measuring light over an eye to be examined, an image processing unit 101 which forms a tomographic image of the eye to be examined from the image data acquired by the data acquisition unit 100, and a display unit 102 which displays the tomographic image of the eye formed by the image processing unit 101.

First, a configuration of the data acquisition unit 100 will be explained.

Figure 2:
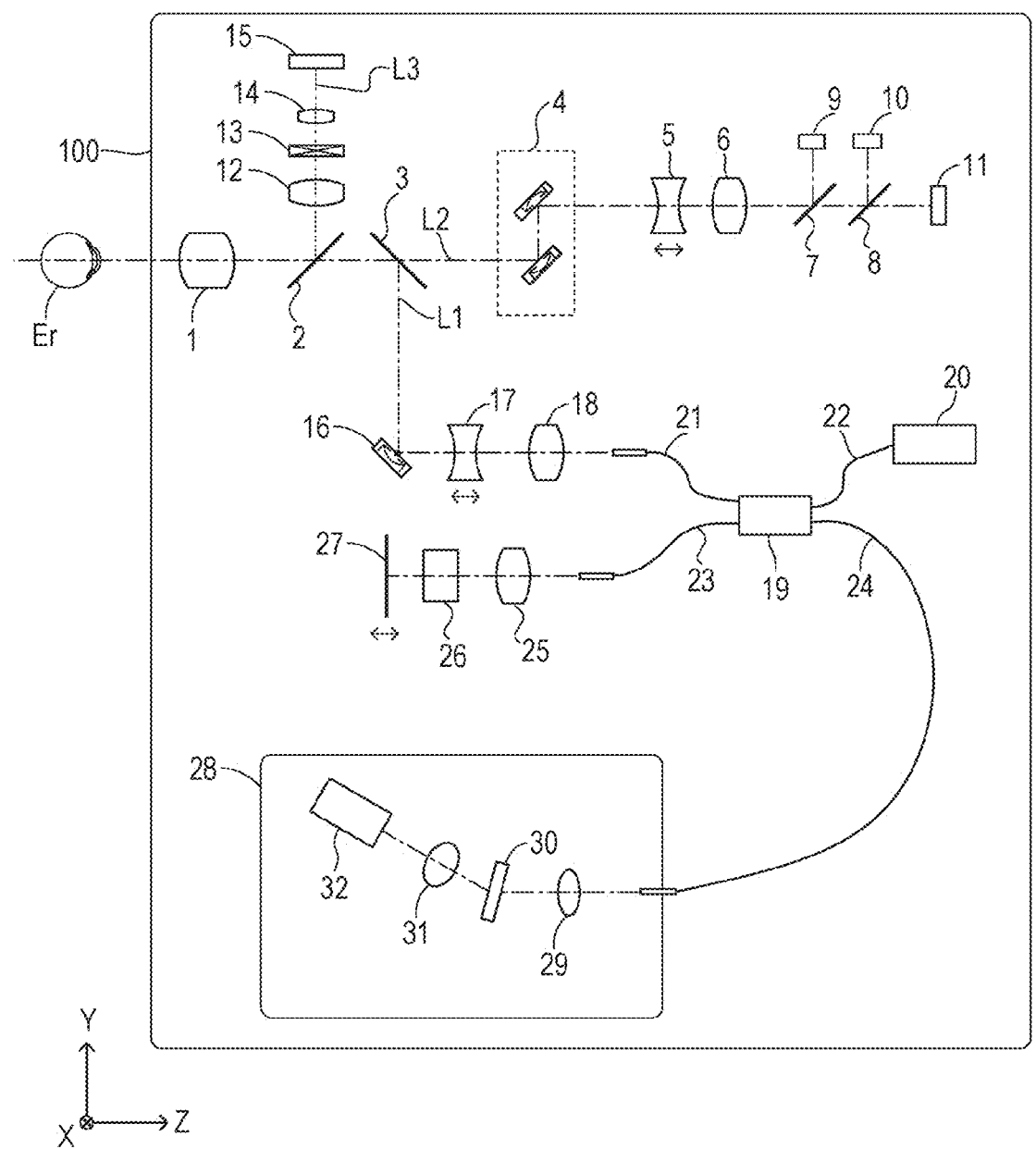
FIG. 2 is a diagram illustrating an example of a configuration of a data acquisition unit.

FIG. 2 illustrates a configuration of the data acquisition unit 100. An objective lens 1 is installed facing an eye Er to be examined, and a first dichroic mirror 2 and a second dichroic mirror 3 are disposed on the optical axis of the objective lens 1. The first dichroic mirror 2 and the second dichroic mirror 3 provide optical paths for individual wavelength ranges: an optical path L1 for an OCT optical system; an optical path L2 for a scanning laser ophthalmoscope (SLO) optical system and a fixation lamp for observation of the eye Er to be examined; and an optical path L3 for observation of an anterior eye portion.

The optical path L2 for the SLO optical system and the fixation lamp includes an SLO scanning unit 4, lenses 5 and 6, a mirror 7, a third dichroic mirror 8, a photodiode 9, an SLO light source 10, and a fixation lamp 11.

The mirror 7 is a prism on which a perforated mirror or a hollow mirror is vapor-deposited. The mirror 7 makes a separation between illumination light from the SLO light source 10 and return light from the eye Er to be examined. The third dichroic mirror 8 makes a separation into the optical paths to the SLO light source 10 and the fixation lamp 11 for individual wavelength ranges.

The SLO scanning unit 4 performs scanning of light emitted from the SLO light source 10 and the fixation lamp 11 over the eye Er to be examined and includes an X scanner for scanning in an X-direction and a Y scanner for scanning in a Y-direction. In the first embodiment, the X scanner needs to perform high-speed scanning. Therefore, the X scanner incudes a polygon mirror. The Y scanner includes a galvanic mirror.

The lens 5 is driven by a motor (not illustrated in FIG. 2) for focusing of the SLO optical system and the fixation lamp 11. The SLO light source 10 produces light having a wavelength of approximately 780 nm. The photodiode 9 detects return light from the eye Er to be examined. The fixation lamp 11 produces visible light to urge a person to be examined to have visual fixation.

The light emitted from the SLO light source 10 is reflected by the third dichroic mirror 8, transmits through the mirror 7, passes through the lenses 5 and 6, and is scanned over the eye Er to be examined by the SLO scanning unit 4. Return light from the eye Er to be examined returns through the same path as projected light. Then, the return light is reflected by the mirror 7 and guided to the photodiode 9.

Light of the fixation lamp 11 transmits through the third dichroic mirror 8 and the mirror 7, passes through the lenses 6 and 5, and is scanned over the eye Er to be examined by the SLO scanning unit 4. At this time, by causing the light of the fixation lamp 11 to blink in association with the movement of the SLO scanning unit 4, any shape is formed at any position over the eye Er to be examined, so that the person to be examined is urged to have visual fixation.

A lens 12, a split prism 13, a lens 14, and a charge-coupled device (CCD) 15 for observation of an anterior eye portion are disposed on the optical path L3 for observation of an anterior eye portion. The CCD 15 has a sensitivity at a wavelength of a light source for observation of an anterior eye portion (not illustrated in FIG. 2), more specifically, at approximately 970 nm.

The split prism 13 is disposed at a position which is conjugate to the pupil of the eye Er to be examined. The split prism 13 is able to detect, as a split image of an anterior eye portion, the distance in a Z-direction (front-back direction) between the eye Er to be examined and the data acquisition unit 100.

An XY scanner 16 and lenses 17 and 18 are disposed on the optical path L1 for the OCT optical system to capture image data of the eye Er to be examined. The XY scanner 16 performs scanning of light from an OCT light source 20 over the eye Er to be examined. The XY scanner 16 is illustrated as a single mirror in FIG. 2. However, the XY scanner 16 is a galvanic mirror which performs scanning in the two-axis directions, that is, X- and Y-directions.

The lens 17 causes light from the OCT light source 20, which is emitted from a fiber 21, to be focused on the eye Er to be examined, and is driven by a motor (not illustrated in FIG. 2). At the same time, by this focusing, return light from the eye Er to be examined forms a spot-like image and is incident to a tip of the fiber 21.

Further, an optical coupler 19, the OCT light source 20, fibers 21 to 24 which are connected and integrated with the optical coupler 19, a lens 25, a dispersion compensation glass 26, a reference mirror 27, a spectroscope 28 are disposed.

Light emitted from the OCT light source 20 via the optical fiber 22 is split at the optical coupler 19 into measuring light and reference light. The measuring light is emitted towards the eye Er to be examined through the optical fiber 21, the optical path L1 for the OCT optical system, and the objective lens 1. The measuring light emitted towards the eye Er to be examined is reflected and scattered at the eye Er to be examined, and reaches the optical coupler 19 through the same optical path.

In contrast, the reference light is emitted via the optical fiber 23 towards the reference mirror 27 through the lens 25 and the dispersion compensation glass 26. The reference light which is reflected by the reference mirror 27 reaches the optical coupler 19 through the same optical path.

The measuring light and the reference light which have reached the optical coupler 19 as described above are combined into interference light. When the optical path length of the measuring light and the optical path length of the reference light become substantially the same, interference occurs. The reference mirror 27 is held by a motor and a driving mechanism (not illustrated in FIG. 2) so as to be adjustable in an optical axis direction, and the optical length of the reference light can be adjusted to the optical length of the measuring light which is variable according to the eye Er to be examined. The interference light is guided to the spectroscope 28 through the optical fiber 24.

The spectroscope 28 includes lenses 29 and 31, a diffractive grating 30, and a line sensor 32. The interference light emitted from the optical fiber 24 turns into parallel light through the lens 29. The parallel light is split by the diffractive grating 30, and forms an image on the line sensor 32 through the lens 31.

In the first embodiment, a Michelson interference system is used as an interference system. However, a Mach-Zehnder interference system may be used. It is preferable to use the systems properly in accordance with a difference in the amount of light between the measuring light and the reference light: the Mach-Zehnder interference system when there is a large difference in the amount of light; and the Michelson interference system when there is a relatively small difference in the amount of light.

Configurations of the image processing unit 101 and the display unit 102 will now be explained.

Figure 3:
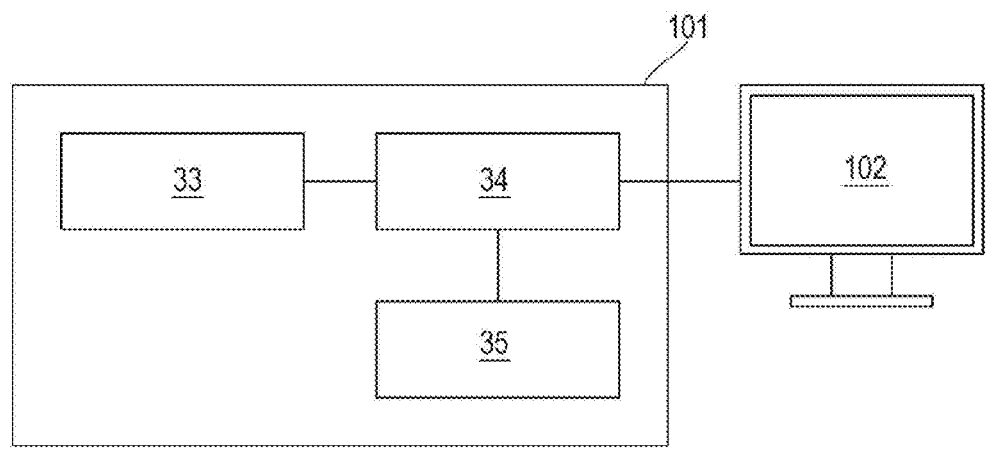
FIG. 3 is a diagram illustrating an example of configurations of an image processing unit and a display unit.

FIG. 3 illustrates configurations of the image processing unit 101 and the display unit 102. The image processing unit 101 includes an image generation part 33, a storage part 34, and an average image generation part 35. The image generation part 33 is connected to the photodiode 9 and the line sensor 32 of the data acquisition unit 100 and the storage part 34 of the image processing unit 101. The image generation part 33 generates an SLO image from plural pieces of data obtained from the photodiode 9 when the eye Er to be examined is scanned with the SLO scanning unit 4 in the X-direction and the Y-direction.

The image generation part 33 also performs Fourier transform of data obtained from the line sensor 32, and by converting the obtained data into brightness or density information, an image is acquired in a depth direction (Z-direction) of the eye Er to be examined. The above-mentioned scanning method is called A scanning, and tomographic images obtained by the A scanning are called A scan images.

By performing the A scanning with the XY scanner 16 in a predetermined transverse direction of the eye Er to be examined, plural A scan images can be obtained. For example, tomographic images on the X-Z plane are obtained by scanning in the X-direction, and tomographic images on the Y-Z plane are obtained by scanning in the Y-direction. A method of scanning the eye Er to be examined in a predetermined transverse direction as described above is called B scanning, and tomographic images obtained by the B scanning are called B scan images.

The storage part 34 is connected to the image generation part 33, the average image generation part 35, and the display unit 102. SLO images and tomographic images obtained from the image generation part 33 or the average image generation part 35 are stored in the storage part 34.

The average image generation part 35 is connected to the storage part 34. The average image generation part 35 obtains plural tomographic images from the storage part 34 and performs averaging processing on the plural tomographic images. The average image generation part 35 is a feature of the present invention and will be explained in detail later. The SLO images and the tomographic images stored in the storage part 34 are displayed on the display unit 102.

Processing from observation to photographing with the optical interference tomography apparatus including the data acquisition unit 100, the image processing unit 101, and the display unit 102 that are described above, will be explained below.

Figure 4:
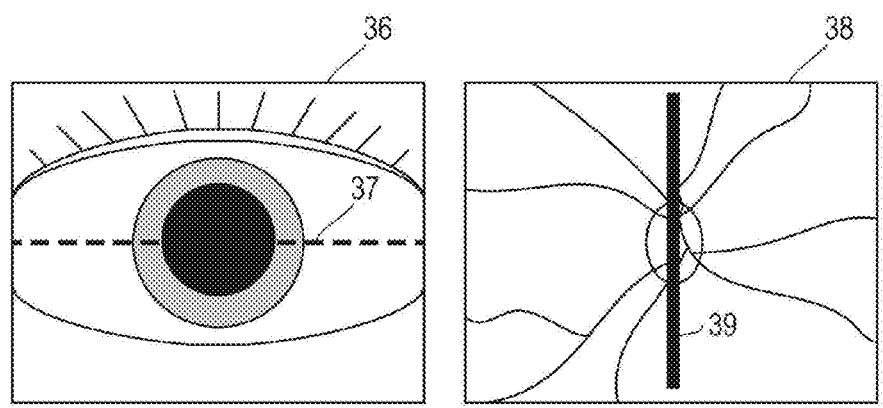
FIG. 4 is a diagram illustrating an example of an anterior eye portion observation image and an SLO image which are displayed on the display unit at the time of observation.

First, an explanation of observation will be provided with reference to FIG. 4. FIG. 4 illustrates an anterior eye portion observation image 36 and an SLO image 38 which are displayed on the display unit 102 at the time of observation. When the eye Er to be examined is positioned in front of the objective lens 1, a photographer performs alignment in the X-, Y-, and Z-directions between the eye Er to be examined and the data acquisition unit 100 by using a joystick (not illustrated in figures) while viewing the anterior eye portion observation image 36. Alignment in the X- and Y-directions is performed such that the center of the pupil of the anterior eye portion observation image 36 is positioned at the center of the screen in which the anterior eye portion observation image 36 is displayed. When alignment in the Z-direction is not appropriate, the anterior eye portion observation image 36 is split along a dotted line 37. Therefore, alignment in the Z-direction is performed such that the anterior eye portion observation image 36 is not split.

When alignment in the X-, Y-, and Z-directions between the eye Er to be examined and the data acquisition unit 100 is completed as described above, the SLO image 38, which is generated by scanning in the X- and Y-directions with the SLO scanning unit 4, is displayed. The anterior eye portion observation image 36 and the SLO image 38 are updated at all times. Thus, the photographer is able to observe the eye Er to be examined, without delay.

Further, a scan line 39 in the SLO image 38 represents a scanning position at which scanning is performed at the time of acquisition of a tomographic image. The scan line 39 is superimposed on the SLO image 38. The photographer performs an operation on the scan line 39 using a scanning position changing unit (not illustrated in figures), such as a mouse or a touch panel, so that a desired scanning position is set. Observation is completed by the above-mentioned operations.

An explanation of photographing will now be provided. When a photographing start button (not illustrated in figures) is operated by the photographer, the data acquisition unit 100 and the image generation part 33 perform scanning along the scan line 39 to generate a B scan image. The B scan image generated by the image generation part 33 is stored in the storage part 34 and displayed on the display unit 102.

Next, the average image generation part 35, which is a feature of the present invention, will be explained taking as an example the case where scanning at the scanning position of the scan line 39 is performed plural times to obtain plural tomographic images for the same position.

Figure 5:
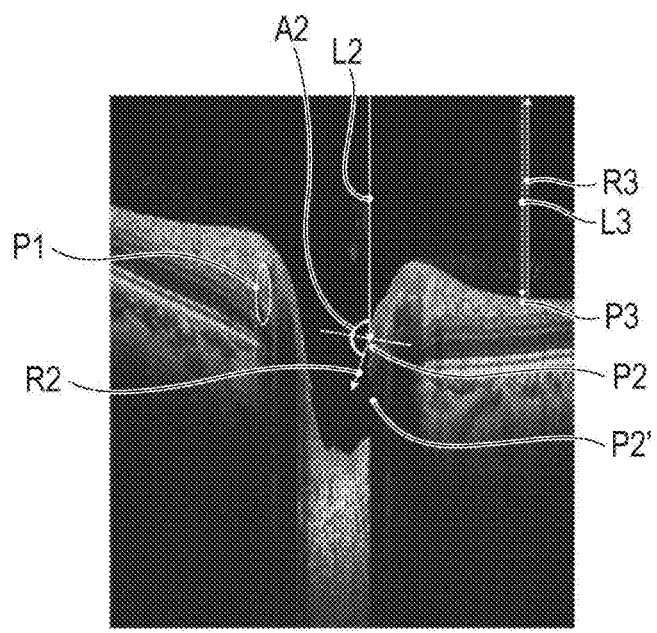
FIG. 5 illustrates an example of measuring light from an OCT light source and reflected scattered light of the measuring light at an eye being examined.

Prior to the explanation of the average image generation part 35, reflected scattered light of the measuring light from the OCT light source 20 at the eye Er to be examined, will be explained with reference to FIG. 5. FIG. 5 is a B scan image of an optic disk rim portion on the scan line 39.

A vitreous body is illustrated in an upper part of FIG. 5. The measuring light from the OCT light source 20 is incident from above. In FIG. 5, P1 represents a blood vessel portion, P2 represents an optic disk rim portion, and P3 represents a retina portion which is other than the optic disk.

First, an explanation of the blood vessel portion P1 will be provided. In the blood vessel portion P1, pulsation of blood vessels, such as constriction and dilation, causes the image brightness to be changed. Therefore, in the case where plural tomographic images for the same position are acquired as in the present invention, the blood vessel portion P1 is rendered in different ways among the tomographic images.

Thus, in the case where a positional difference is detected using a template in which the blood vessel portion P1 extends over a wide range, the similarity calculated is low (the difference calculated is high) even though there is no positional difference.

Next, when attention is paid to the optic disk rim portion P2, the image brightness of the optic disk rim portion P2 is low in FIG. 5. Further, when a target is set to P2', which is positioned deeper (lower, in FIG. 5) than the optic disk rim portion P2, the target is hardly rendered.

This is because when the measuring light from the OCT light source 20 for performing A scanning of the optic disk rim portion P2 is represented by L2, reflected scattered light of the measuring light L2 in the optic disk rim portion P2 is the strongest in a specular reflection direction R2, and on the other hand, reflected scattered light in the direction of the data acquisition unit 100, which is located in the upper part of FIG. 5, is weak. The specular reflection direction is determined according to an incidence angle A2, which is an angle formed by the normal line of the optic disk rim portion P2 and the measuring light L2.

In the case where the incidence angle of the measuring light relative to a target at the time of A scanning is large, the image brightness of the target rendered by the A scanning is low. The state where the image brightness of the target is low means that the target is susceptible to noise generated by a laser speckle or the line sensor 32.

Therefore, when a positional difference is detected using a template in which a target rendered with a large incidence angle of measuring light at the time of A scanning, such as the optic disk rim portion P2, extends over a wide range, the similarity calculated is low (the difference calculated is high) even though there is no positional difference.

In contrast to the optic disk rim portion P2, the retina portion P3 other than the optic disk has a small incidence angle formed by measuring light and a target at the time of A scanning. In FIG. 5, L3 represents measuring light from the OCT light source 20 for measuring the retina portion P3 other than the optic disk, and R3 represents reflected scattered light of the measuring light L3 in the specular reflection direction in the retina portion P3 other than the optic disk.

The reflected scattered light R3 of the measuring light L3 in the specular reflection direction in the retina portion P3 other than the optic disk travels towards the data acquisition unit 100, which is positioned in the upper part of FIG. 5. Therefore, the image brightness of the obtained tomographic image is high, and the cross-section of the retina portion is clearly rendered.

Consequently, in the case where a positional difference is detected using a template in which a target rendered with a small incidence light of measuring light at the time of A scanning, such as the retina portion P3 other than the optic disk, extends over a wide range, the similarity is low when there is a positional difference, and on the other hand, the similarity is high when there is no positional difference.

In the case where a target in which a change of the image brightness occurs, such as the blood vessel portion P1, or a target rendered with a large incidence angle of measuring light at the time of A scanning, such as the optic disk rim portion P2, extends over a wide range of a template, even if there is no positional difference, the similarity calculated is low (the difference calculated is high). Therefore, the case where there is no positional difference cannot be distinguished from the case where there is a positional difference, and the accuracy in the detection of a positional difference is thus deteriorated.

Although the fact that the similarity is low in the case where a target extends over a wide range of a template has been described above, even if the target does not extend over a wide range, the similarity becomes lower in accordance with the proportion of the target in the template.

Figure 6:
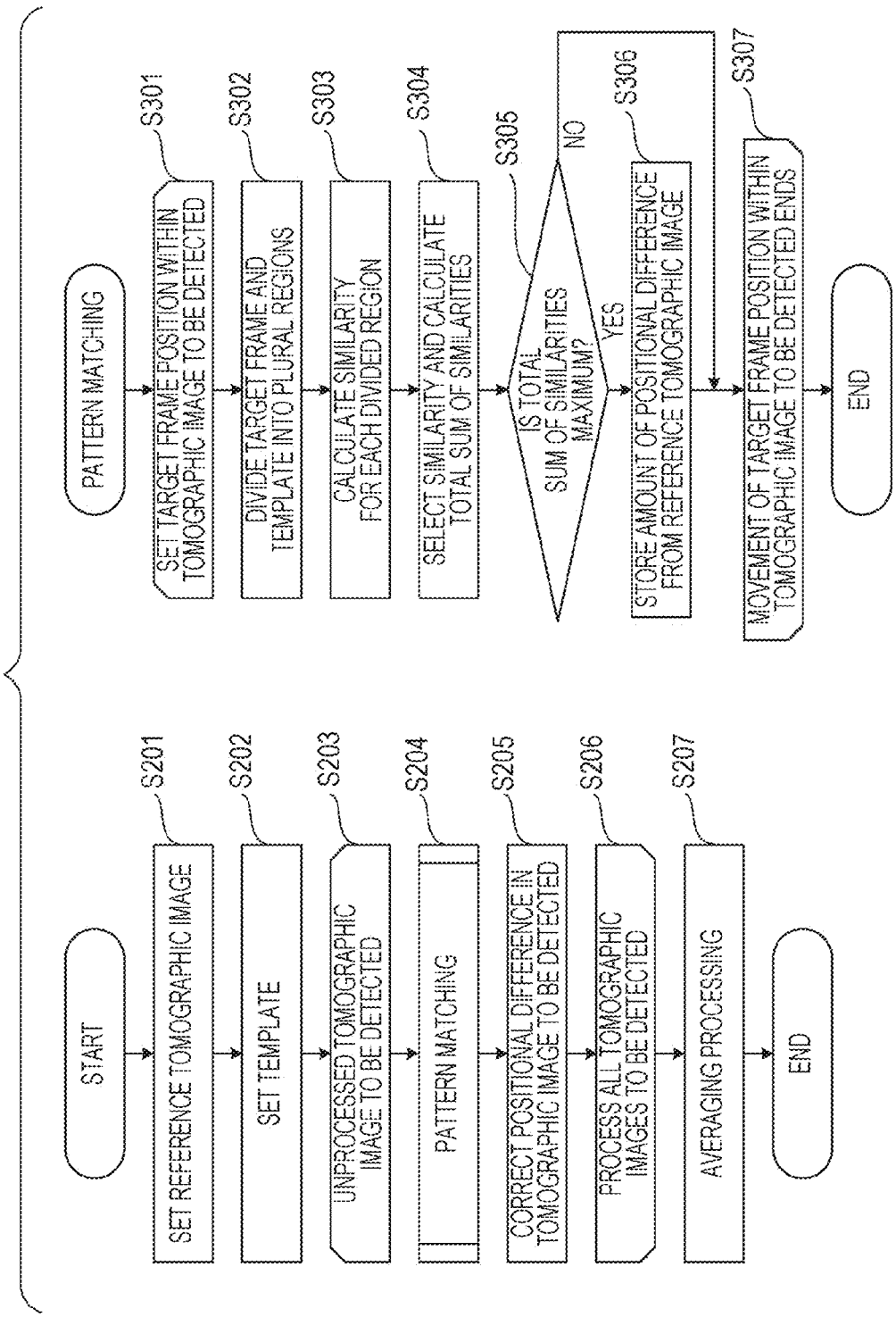
FIG. 6 is a flowchart illustrating an example of a process of an average image generation part in a first embodiment.

Next, the average image generation part 35, which is a feature of the present invention, will be explained with reference to FIG. 6. FIG. 6 is a flowchart illustrating the flow of a process of the average image generation part 35.

When scanning of the scanning position of the scan line 39 is performed plural times and plural tomographic images for the same position are obtained, the average image generation part 35 selects one of the obtained plural tomographic images and sets the selected tomographic image as a reference tomographic image. The remaining tomographic images other than the reference tomographic image are set as tomographic images to be detected (step S201).

Figure 7:
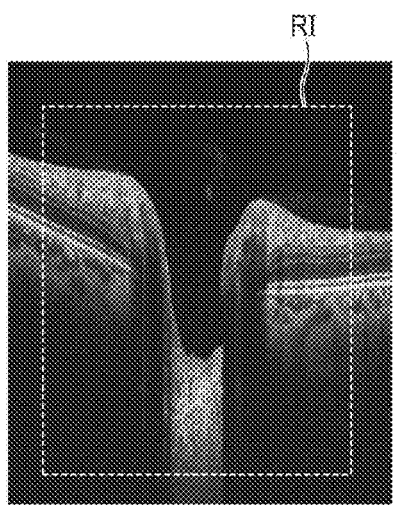
FIG. 7 illustrates an example of a template used in pattern matching.

Next, a template is set from the reference tomographic image set in step S201. FIG. 7 illustrates the reference tomographic image and the template set within the reference tomographic image. In FIG. 7, a dotted line part RI represents the template. The template RI is used to detect a positional difference at the time of pattern matching.

The case where the image brightness of a tomographic image is used for the template RI is used as an example of the present invention. However, an extracted feature of an image, such as edge information of a tomographic image, may be used as a template (step S202).

Processing from steps S203 to S206 is repeated until processing of steps S204 and S205 is performed for all the tomographic images to be detected.

Processing of step S204 is pattern matching. The details of pattern matching are explained in steps S301 to S307. Processing of steps S302 to S304 represents a method for calculating similarity, which is calculated based on the template RI and a tomographic image to be detected within a target frame TI. Similarity is calculated by the image processing unit 101. That is, the image processing unit 101 corresponds to an example of a determining unit configured to determine a similarity.

Figure 8:
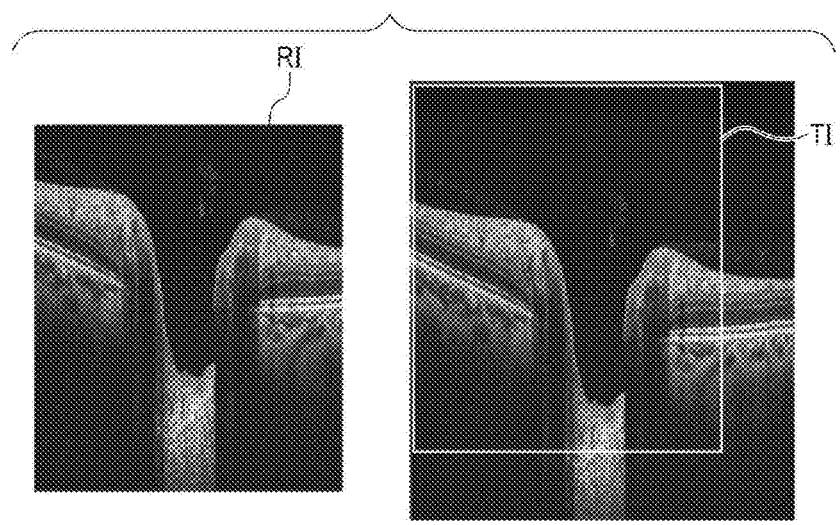
FIG. 8 is a diagram illustrating an example of a target frame which is disposed at a predetermined position within a tomographic image to be detected in the first embodiment.

First, in step S301, the target frame TI having the same size as the template RI is set at a predetermined position within a tomographic image to be detected, as illustrated in FIG. 8. The target frame TI sequentially moves within the tomographic image to be detected when the processing of steps S302 to S306, which will be described later, is performed.

Next, the processing of steps S302 to S304 will be explained.

In step S302, the template RI and the tomographic image to be detected within the target frame TI are each divided into plural regions. For explanation, the case where the template RI and the target frame TI are each divided into twelve regions is illustrated as an example in FIG. 9. Since a tomographic image is a collection of A scanning results, the division is performed in the scanning direction of the OCT light source 20.

In step S303, the similarity is calculated for each of the regions obtained by the division in step S302. Similarities of corresponding regions between the template RI and the tomographic image to be detected within the target frame TI, such as the similarity between RI1 and il1 and the similarity between RI2 and TI2, are calculated. In this case, similarity between twelve regions (twelve similarities) is calculated.

Next in step S304, a predetermined number of similarities (or similar regions) are selected from among the plural similarities obtained in step S303. That is, some of the obtained similarities are selected. A preset (predetermined) number of similarities are selected in a descending order of similarity, and the total sum of the selected similarities is calculated.

Effects similar to those described above may be achieved when, instead of selecting the preset predetermined number of similarities, regions having similarity equal to or higher than a predetermined value are selected.

Further, effects similar to those described above may be achieved when a preset predetermined number of similarities are selected from the regions having similarities equal to or higher than the predetermined value.

Furthermore, effects similar to those described above may be achieved when, instead of selecting the preset predetermined number of similarities, weighting is performed on the similarities in accordance with the similarities of the regions and the total sum of the similarities is calculated. For example, a higher weighting value is assigned to a higher similarity, and a lower weighting value is assigned to a lower similarity.

Figure 9:
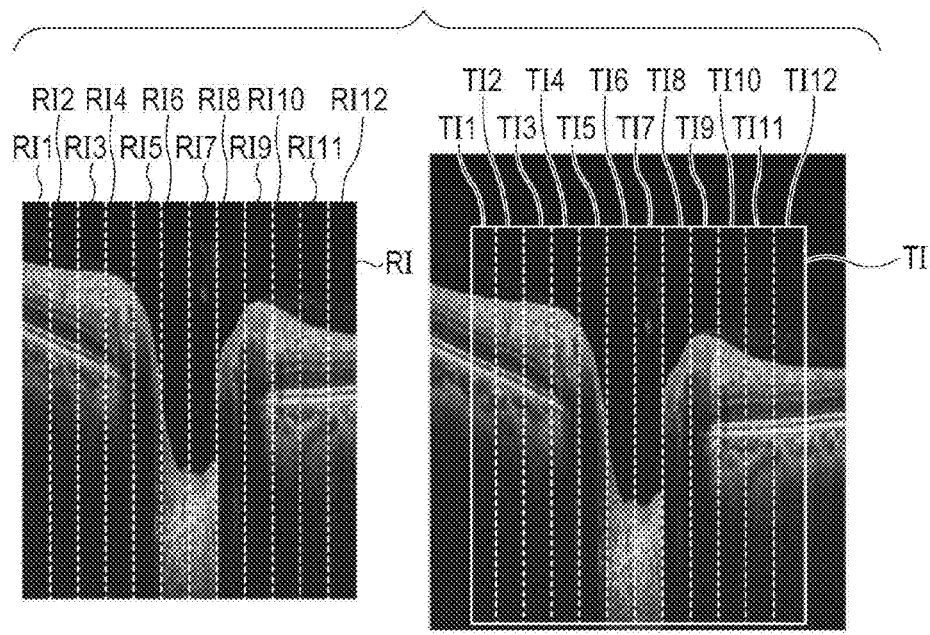
FIG. 9 is a diagram illustrating an example of a case where a pattern the same as the template exists within the target frame in the tomographic image to be detected.
Figure 10:
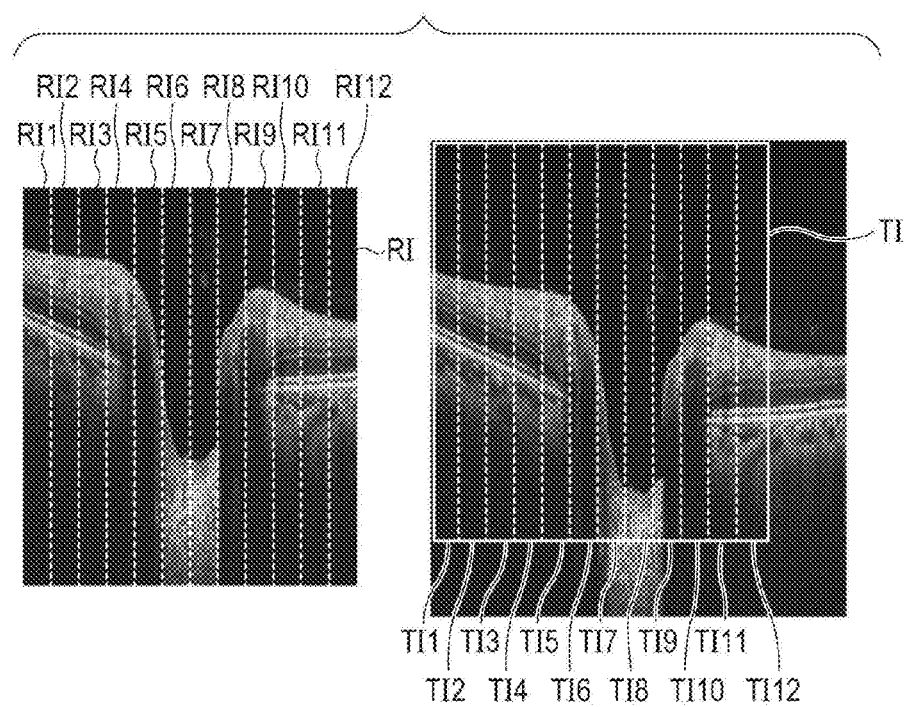
FIG. 10 is a diagram illustrating an example of a case where a pattern different from the template exists within the target frame in the tomographic image to be detected.

FIGS. 9 and 10 illustrate two cases where the positions of the target frames TI are different. FIG. 9 illustrates the case where the same pattern as the template RI exists in the tomographic image to be detected within the target frame TI. In contrast, FIG. 10 illustrates the case where a pattern different from the template RI exists in the tomographic image to be detected within the target frame TI.

In the case where a pattern different from the template RI exists in the tomographic image to be detected within the target frame TI as illustrated in FIG. 10, each of the similarities of the individual regions obtained in step S303 is low due to a positional difference. Accordingly, the total sum of the similarities obtained after the selection in step S304 is also low.

In contrast, in the case where the same pattern as the template RI exists in the tomographic image to be detected within the target frame TI as illustrated in FIG. 9, among the similarities of the regions obtained in step S303, the similarities between RI4 and TI4, and between RI9 and TI9, where a blood vessel portion rendered in the region is large, are low even though there is no positional difference. Further, the similarities between RI5 and TI5, and between RI8 and TI8, where a target rendered with a large incidence angle of measuring light at the time of A scanning, in the first embodiment, an optic disk rim portion, extends largely in the region, are low even though there is no positional difference. The similarities of the other regions are high because there is no positional difference.

In the case of FIG. 9, the blood vessel portion (RI4 and TI4, RI9 and TI9) and a target rendered with a large incidence angle of measuring light at the time of A scanning, in the first embodiment, the optic disk rim portion (RI5 and TI5, and RI8 and TI8), are excluded in step S304. Therefore, the obtained total sum of the similarities is high.

Then, in steps S305 and S306, when the total sum of the similarities in the tomographic image to be detected is maximum, the amount of positional difference from the reference tomographic image is calculated and stored.

The amount of positional difference from the reference tomographic image in the case where the total sum of the similarities is maximum is searched for, while sequentially moving the position of the target frame TI within the tomographic image to be detected, as described above. When all the searching for the tomographic image to be detected is completed, the pattern matching is ended (step S307).

When the pattern matching in step S204 is ended, the positional difference in the tomographic image to be detected is corrected in step S205, in accordance with the amount of positional difference between the reference tomographic image and the tomographic image to be detected obtained in step S306. The positional difference from the reference tomographic image is eliminated by performing displacement, such as translation of the entire tomographic image to be detected based on the amount of positional difference. That is, the entire tomographic image is moved relative (with respect) to the reference image.

When the processing of steps S203 to S206 is performed for all the tomographic images to be detected, averaging processing is performed in step S207 by performing addition and division for each pixel of the reference tomographic image and all the tomographic images to be detected. Since exactly the same region cannot be photographed because of involuntary eye movement of an eye to be examined, when a similarity obtained in step S304 is lower than or equal to a predetermined value, the similarity is excluded from the averaging processing performed in step S207.

In the case where an amount of positional difference between the reference tomographic image and a tomographic image to be detected obtained in processing of steps S301 to S307 is equal to or larger than a predetermined value, the amount of positional difference may be excluded from the averaging processing performed in step S207.

Although the template RI and the target frame TI are each divided into plural regions in steps S302 and S303, it should be noted that the division is performed not to obtain the positional differences among the divided regions but to obtain the positional difference between the template RI and the target frame TI. Therefore, for example, division into regions is not performed in, for example, step S301, which is different from steps S302 and S303.

By the processing of steps S302 to S304, which is a feature of the present invention, a target which causes a reduction in the similarity even though there is no positional difference and thus makes it difficult to make a distinction from the case where there is a positional difference, can be selectively excluded. Therefore, the similarity obtained represents only the positional difference between the template RI and the target frame TI. Consequently, high-accuracy detection of a positional difference can be achieved.

In addition, by selectively excluding a target which causes a reduction in the similarity even though there is no positional difference, the similarity obtained is high. Therefore, the number of cases where a similarity which is lower than or equal to a predetermined value is excluded from averaging processing, decreases. Accordingly, the number of tomographic images which are subjected to averaging processing can be increased, and a tomographic image with reduced noise can thus be provided.

Although the example in which the target frame TI is sequentially moved within a tomographic image to be detected has been explained in the first embodiment, rotation processing may be performed in addition to the movement.

Although the example in which the data acquisition unit 100, the image processing unit 101, and the display unit 102 are disposed separately from one another, has been explained in the first embodiment, the data acquisition unit 100, the image processing unit 101, and the display unit 102 may be accommodated within one housing.

The image processing unit 101 according to the first embodiment may be implemented by a personal computer.

Second Embodiment

Figure 11:
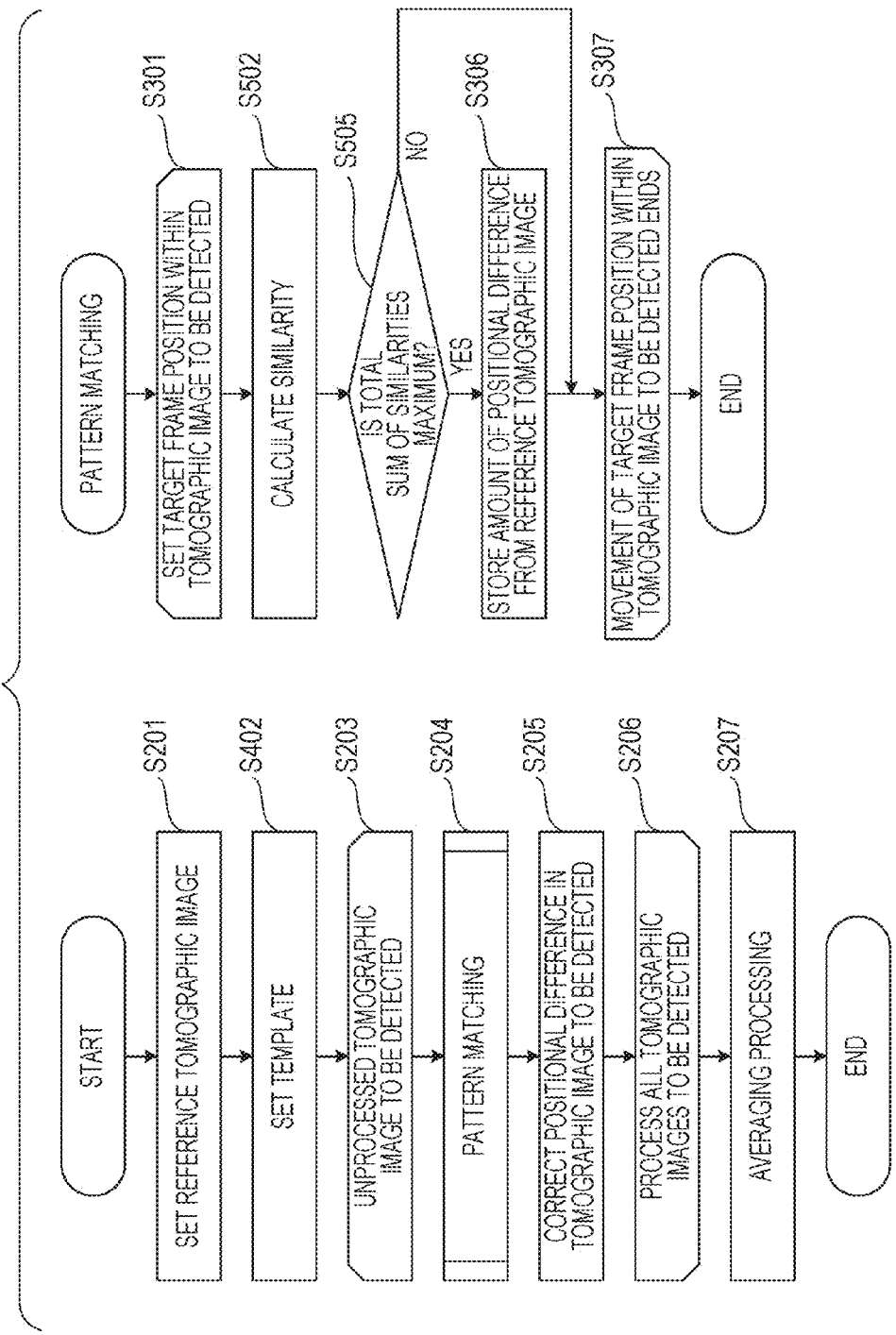
FIG. 11 is a flowchart illustrating an example of a process of an average image generation part in a second embodiment.

A configuration according to a second embodiment is substantially the same as that illustrated in FIGS. 1 to 3 of the first embodiment. The second embodiment differs from the first embodiment in the processing flowchart which illustrates the flow of a process of the average image generation part 35, and the flowchart illustrating the flow of the process of the average image generation part 35 according to the second embodiment is illustrated in FIG. 11. In the flowchart illustrated in FIG. 11, the same processes (steps) as those in the first embodiment are assigned the same numbers. In the second embodiment, step S202 in the first embodiment is replaced with step S402, steps S302 to S304 in the first embodiment are replaced with step S502, and step S305 in the first embodiment is replaced with step S505.

The method of observation and photographing is similar to that in the first embodiment, and the explanation of the method of observation and photographing will be omitted to obviate unnecessary repetition.

When a reference tomographic image is set in step S201, a template is set in step S402. A target which causes a change in the image brightness, such as the blood vessel portion P1, or a target rendered with a large incidence angle of measuring light at the time of A scanning, such as the optic disk rim portion P2, exists within the template RI set within the reference tomographic image in the first embodiment. However, in the second embodiment, such a target is excluded from the template RI in step S402. In order to make a distinction from the target RI used in the first embodiment, the template used in the second embodiment will be represented by RI'.

Figure 12:
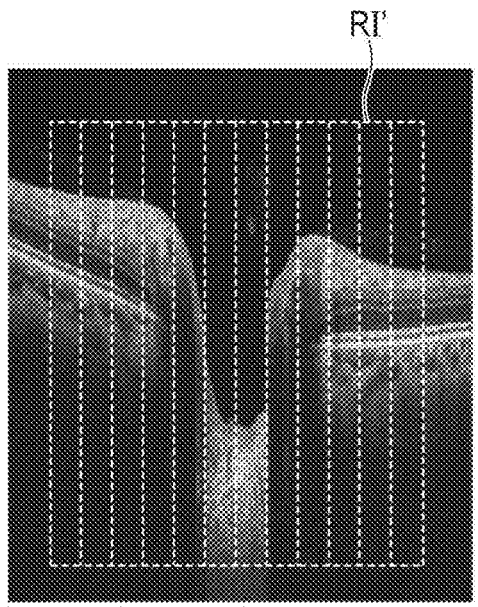
FIG. 12 is a diagram illustrating an example of a template which is divided into plural regions.

In more detail, first, the template RI' is set within the reference tomographic image, as in step S201 of the first embodiment. Then, the sum of the image brightnesses of each of plural regions obtained by division of the template RI', is obtained. FIG. 12 illustrates the template RI' which is divided into plural regions. In FIG. 12, the case where the template RI' is divided into twelve regions is illustrated.

A predetermined number of regions are selected in a descending order of the sum of the image brightnesses obtained for each region. The number of regions to be selected is set in advance. Since a tomographic image is a collection of A scanning results, the division is performed in the scanning direction of the OCT light source 20.

Figure 13:
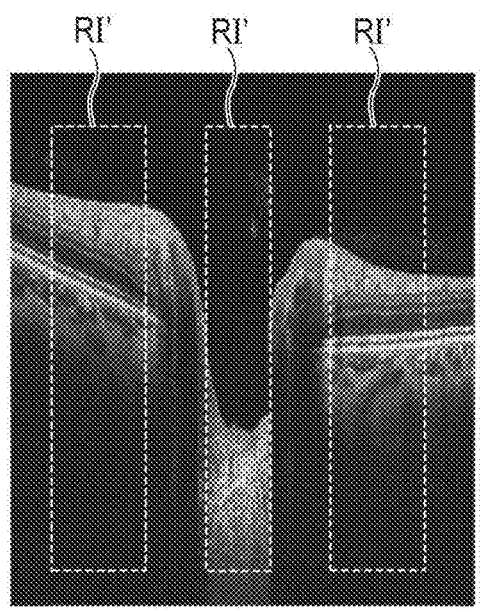
FIG. 13 is a diagram illustrating an example of the template set in step S402.

In the case where a divided region adjacent to a selected divided region is also selected, the divided regions are combined together. Then, the template RI' illustrated in FIG. 13 is set. As is clear from FIG. 13, the vessel portion and a target rendered with a large incidence angle of measuring light at the time of A scanning, in this case, the optic disk rim portion, are excluded.

In the blood vessel portion, only a change in the image brightness occurs due to pulsation of blood vessels, such as constriction and dilation, and the image brightness is not low. However, a portion deeper (lower, in FIG. 13) than the blood vessel portion has a low image brightness. Therefore, in the case where a divided region includes a blood vessel portion, the sum of the image brightnesses of the region is low. The reason why the image brightness of a target rendered with a large incidence angle of measuring light at the time of A scanning, in this case, the optic disk rim portion, is low is as explained in the first embodiment. Therefore, the redundant explanation will be omitted here.

Instead of selecting a preset predetermined number of regions, regions having image brightnesses equal to or higher than a predetermined value may be selected.

A low image brightness means a low image edge intensity. Therefore, instead of calculating the sum of image brightnesses, the sum of image edge intensities may be calculated. For calculation of an image edge, a scanning direction component of the OCT light source 20 is detected, and a one-dimensional differentiation filter is used.

By excluding a target which causes a change in the image brightness, such as the blood vessel portion P1, or a target rendered with a large incidence angle of measuring light at the time of A scanning, such as the optic disk rim portion P2, from the template RI' as described above, the processing of steps S302 to S304 in the first embodiment becomes unnecessary, and effects equivalent to those in the first embodiment can be attained.

Processing of steps S203 to S206 is repeated until steps S204 and S205 are performed for all the tomographic images to be detected.

Step S204 is pattern matching. The details of pattern matching are described in steps S301 and S502, step S505, and steps S306 to S307.

Figure 14:
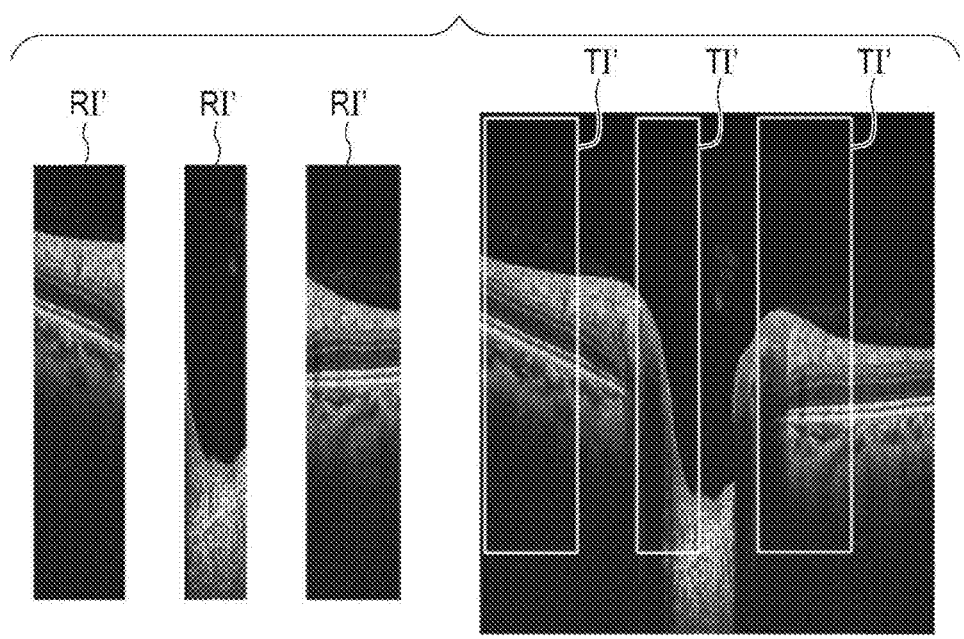
FIG. 14 is a diagram illustrating an example of the target frame which is disposed at a predetermined position within a tomographic image to be detected in the second embodiment.

In step S301, a target frame TI' having the same size as the template RI' is set at a predetermined position within the tomographic image to be detected, as illustrated in FIG. 14. In order to make a distinction from the target frame TI used in the first embodiment, the target frame used in the second embodiment is represented by TI'.

When steps S502 and S505, which will be described later, and step S306 are performed, the target frame TI' is sequentially moved within the tomographic image to be detected. As illustrated in FIG. 14, the target frame TI' is positioned at three separate positions. The target frame TI' is moved while keeping the positional relationship among the three positions. The three positions are not moved independently.

Then, in step S502, the similarity between the template RI' and the tomographic image to be detected within the target frame TI' is calculated. Although the total sum of similarities is obtained in the first embodiment, only one similarity is calculated in the second embodiment.

Then, in steps S505 and S306, when the similarity within the tomographic image to be detected is highest, the amount of positional difference from the reference tomographic image is calculated and stored.

The amount of positional difference from the reference tomographic image in the case where the similarity is highest is searched for, while moving the position of the target frame TI' within the tomographic image to be detected, as described above. When all the searching within the tomographic image to be detected is completed, the pattern matching is ended (step S307).

When the pattern matching in step S204 is ended, the positional difference in the tomographic image to be detected is corrected in step S205. When steps S204 and S205 are performed for all the tomographic images to be detected, averaging processing is performed in step S207.

Since a target which causes a reduction in the similarity even though there is no positional difference and thus makes it difficult to make a distinction from the case where there is a positional difference, is excluded from the template RI' in advance in step S402, the similarity obtained represents only a positional difference. Therefore, a tomographic image obtained after averaging processing is performed achieves effects similar to those in the first embodiment.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-221090, filed Oct. 24, 2013, which is hereby incorporated by reference herein in its entirety.

What is claimed is:

1. An image processing apparatus comprising:
an acquiring unit configured to acquire a first tomographic image and a second tomographic image;
a dividing unit configured to divide the first tomographic image and the second tomographic image into plural regions respectively;
a determining unit configured to determine similarity for each of the plural regions by comparing the plural regions in the first tomographic image with the plural regions in the second tomographic image;
a selecting unit configured to select a part of similarities in the plural regions, on the basis of the similarities in the plural regions; and
a registration unit configured to perform registration between the first tomographic image and the second tomographic image, on the basis of the part of similarities selected by the selecting unit.

2. The image processing apparatus according to claim 1, wherein the selecting unit selects a predetermined number of similarities from among similarities in the plural regions.

3. The image processing apparatus according to claim 2, wherein the selecting unit selects similarities having a predetermined value or greater from among the similarities in the plural regions.

4. The image processing apparatus according to claim 3, wherein the registration unit moves the second tomographic image relative to the first tomographic image so that the total sum of the part of similarities selected by the selecting unit becomes maximum.

5. The image processing apparatus according to claim 3, wherein the registration unit moves the entire second tomographic image relative to the first tomographic image so that the total sum of the part of similarities selected by the selecting unit becomes maximum.

6. The image processing apparatus according to claim 2, wherein the registration unit moves the second tomographic image relative to the first tomographic image so that the total sum of the part of similarities selected by the selecting unit becomes maximum.

7. The image processing apparatus according to claim 2, wherein the registration unit moves the entire second tomographic image relative to the first tomographic image so that the total sum of the part of similarities selected by the selecting unit becomes maximum.

8. The image processing apparatus according to claim 1, wherein the selecting unit selects similarities having a predetermined value or greater from among the similarities in the plural regions.

9. The image processing apparatus according to claim 8, wherein the registration unit moves the second tomographic image relative to the first tomographic image so that the total sum of the part of similarities selected by the selecting unit becomes maximum.

10. The image processing apparatus according to claim 8, wherein the registration unit moves the entire second tomographic image relative to the first tomographic image so that the total sum of the part of similarities selected by the selecting unit becomes maximum.

11. The image processing apparatus according to claim 1, wherein the registration unit moves the second tomographic image relative to the first tomographic image so that the total sum of the part of similarities selected by the selecting unit becomes maximum.

12. The image processing apparatus according to claim 1, wherein the registration unit moves the entire second tomographic image relative to the first tomographic image so that the total sum of the part of similarities selected by the selecting unit becomes maximum.

13. An image processing apparatus comprising:
an acquiring unit configured to acquire a first tomographic image and a second tomographic image;
a dividing unit configured to divide the first tomographic image and the second tomographic image into plural regions respectively;
a determining unit configured to determine a similarity for each of the plural regions by comparing the plural regions in the first tomographic image with the plural regions in the second tomographic image; and
a registration unit configured to perform registration between the first tomographic image and the second tomographic image, on the basis of the similarities on which weighting has been performed in accordance with a degree of the similarities.

14. The image processing apparatus according to claim 13, wherein a higher weighting value is assigned to a higher similarity.

15. The image processing apparatus according to claim 14, wherein the registration unit moves the second tomographic image relative to the first tomographic image so that the total sum of similarities becomes maximum.

16. The image processing apparatus according to claim 13, wherein the registration unit moves the second tomographic image relative to the first tomographic image so that the total sum of similarities becomes maximum.

17. The image processing apparatus according to claim 13, wherein the registration unit moves the entire second tomographic image relative to the first tomographic image so that the total sum of similarities becomes maximum.

18. An image processing method comprising:
   an acquiring step of acquiring a first tomographic image and a second tomographic image;
   a dividing step of dividing the first tomographic image and the second tomographic image into plural regions respectively;
   a determining step of determining a similarity for each of the plural regions by comparing the plural regions in the first tomographic image with the plural regions in the second tomographic image;
   a selecting step of selecting a part of similarities in the plural regions, on the basis of the similarities in the plural regions; and
   a registration step of performing registration between the first tomographic image and the second tomographic image, on the basis of the part of similarities selected by the selecting step.

19. A non-transitory storage medium storing a program for causing a computer to execute the steps of the image processing method according to claim 18.

20. An image processing apparatus comprising:
   an acquiring unit configured to acquire a first tomographic image and a second tomographic image;
   a selecting unit configured to select, based on the image brightnesses of the first tomographic image, a first region in the first tomographic image where image brightnesses are higher than image brightnesses of a second region in the first tomographic image;
   a determining unit configured to determine similarity by comparing the first region in the first tomographic image with a region in the second tomographic image corresponding to the first region; and
   a registration unit configured to perform registration between the first tomographic image and the second tomographic image, on the basis of the similarity determined by the determining unit.

21. The image processing apparatus according to claim 20, wherein the second region includes an optic disk rim portion; and
   the selecting unit does not select the second region.

22. The image processing apparatus according to claim 20, wherein the selecting unit does not select the second region.

23. An image processing apparatus comprising:
   an acquiring unit configured to acquire a first tomographic image and a second tomographic image;
   a dividing unit configured to divide the first tomographic image into plural regions;
   a determining unit configured to determine similarity for the plural regions by comparing the plural regions in the first tomographic image with regions in the second tomographic image corresponding to the plural regions;
   a selecting unit configured to select a part of similarities in the plural regions, on the basis of the similarities in the plural regions; and
   a registration unit configured to perform registration between the first tomographic image and the second tomographic image, on the basis of the part of similarities selected by the selecting unit.

24. The image processing apparatus according to claim 23, wherein the selecting unit selects a predetermined number of similarities from among similarities in the plural regions.

25. The image processing apparatus according to claim 24, wherein the selecting unit selects similarities having a predetermined value or greater from among the similarities in the plural regions.

26. The image processing apparatus according to claim 24, wherein the registration unit moves the second tomographic image relative to the first tomographic image so that the total sum of the part of similarities selected by the selecting unit becomes maximum.

27. The image processing apparatus according to claim 23, wherein the selecting unit selects similarities having a predetermined value or greater from among the similarities in the plural regions.

28. The image processing apparatus according to claim 23, wherein the registration unit moves the second tomographic image relative to the first tomographic image so that the total sum of the part of similarities selected by the selecting unit becomes maximum.

* * * * *